(12) United States Patent
Samuel

(10) Patent No.: US 8,246,657 B1
(45) Date of Patent: Aug. 21, 2012

(54) SPINAL CROSS CONNECTOR

(75) Inventor: Forrest Samuel, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 64 days.

(21) Appl. No.: 12/826,590

(22) Filed: Jun. 29, 2010

Related U.S. Application Data

(60) Provisional application No. 61/221,525, filed on Jun. 29, 2009, provisional application No. 61/233,287, filed on Aug. 12, 2009.

(51) Int. Cl.
*A61B 17/70* (2006.01)
(52) U.S. Cl. .................................. 606/250; 606/278
(58) Field of Classification Search .............. 606/260, 606/278, 250–253, 259
See application file for complete search history.

(56) References Cited

U.S. PATENT DOCUMENTS

| | | |
|---|---|---|
| 3,012,091 A | 12/1961 | Schiffmann |
| 5,084,049 A | 1/1992 | Asher et al. |
| 5,092,893 A | 3/1992 | Smith |
| 5,397,363 A | 3/1995 | Gelbard |
| 5,498,263 A | 3/1996 | DiNello et al. |
| 5,522,816 A | 6/1996 | Dinello et al. |
| 5,569,246 A | 10/1996 | Ojima et al. |
| 5,601,554 A | 2/1997 | Howland et al. |
| 5,624,442 A | 4/1997 | Mellinger et al. |
| 5,669,910 A | 9/1997 | Korhonen et al. |
| 5,676,703 A | 10/1997 | Gelbard |
| 5,688,272 A | 11/1997 | Montague et al. |
| 5,693,053 A | 12/1997 | Estes |
| 5,702,393 A | 12/1997 | Pfaifer |
| 5,934,818 A | 8/1999 | Schmitt et al. |
| 5,947,966 A | 9/1999 | Drewry et al. |
| 5,980,521 A | 11/1999 | Montague et al. |
| 5,980,523 A | 11/1999 | Jackson et al. |
| 6,083,226 A | 7/2000 | Fiz et al. |
| 6,113,600 A | 9/2000 | Drummond et al. |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,217,578 B1 | 4/2001 | Crozet et al. |
| 6,234,705 B1 | 5/2001 | Troxell |
| 6,238,396 B1 | 5/2001 | Lombardo |
| 6,280,445 B1 | 8/2001 | Morrison et al. |
| 6,283,967 B1 | 9/2001 | Troxell et al. |
| 6,306,137 B2 | 10/2001 | Troxell |
| 6,328,740 B1 | 12/2001 | Richelsoph |
| 6,328,741 B1 | 12/2001 | Richelsoph |
| 6,402,751 B1 | 6/2002 | Hoeck et al. |
| 6,413,258 B1 | 7/2002 | Bernhardt, Jr. |
| 6,485,491 B1 | 11/2002 | Farris et al. |
| 6,524,310 B1 | 2/2003 | Lombardo et al. |

(Continued)

FOREIGN PATENT DOCUMENTS

EP 0746255 B1 9/2002

(Continued)

*Primary Examiner* — Eduardo C Robert
*Assistant Examiner* — Christina Negrelli
(74) *Attorney, Agent, or Firm* — Jonathan Spangler; Rory Schermerhorn

(57) ABSTRACT

The present application describes a spinal cross-connector and related methods for augmenting and stiffening spinal fixation constructs. The cross connector may include multiple rod-stabilization members that simultaneously engage respective rods of a fixation construct. Simultaneous engagement by the rod-stabilization members may be effectuated by a single locking step.

8 Claims, 5 Drawing Sheets

U.S. PATENT DOCUMENTS

| | | | |
|---|---|---|---|
| 6,554,832 B2 | 4/2003 | Shluzas | |
| 6,602,253 B2 | 8/2003 | Richelsoph et al. | |
| 6,616,668 B2 | 9/2003 | Altarac et al. | |
| 6,641,583 B2 | 11/2003 | Shluzas et al. | |
| 6,699,248 B2 | 3/2004 | Jackson | |
| 6,736,817 B2 | 5/2004 | Troxell et al. | |
| 6,752,807 B2 | 6/2004 | Lin et al. | |
| 6,761,721 B2 | 7/2004 | Burgess et al. | |
| 6,783,526 B1 | 8/2004 | Lin et al. | |
| 6,872,208 B1 | 3/2005 | McBride et al. | |
| 6,875,211 B2 | 4/2005 | Nichols et al. | |
| 6,887,241 B1 | 5/2005 | McBride et al. | |
| 6,958,066 B2 | 10/2005 | Richelsoph et al. | |
| 6,960,212 B2 | 11/2005 | Richelsoph et al. | |
| 7,029,474 B2 | 4/2006 | Richelsoph et al. | |
| 7,066,938 B2 | 6/2006 | Slivka et al. | |
| 7,083,622 B2 | 8/2006 | Simonson | |
| 7,104,993 B2 | 9/2006 | Baynham et al. | |
| 7,122,036 B2 | 10/2006 | Vanacker | |
| 7,137,986 B2 | 11/2006 | Troxell et al. | |
| 7,250,052 B2 | 7/2007 | Landry et al. | |
| 7,481,827 B2 | 1/2009 | Ryan et al. | |
| 7,628,799 B2 | 12/2009 | Richelsoph et al. | |
| 7,645,294 B2 | 1/2010 | Kalfas et al. | |
| 7,695,500 B2 | 4/2010 | Markworth | |
| 7,717,938 B2 | 5/2010 | Kim et al. | |
| 7,744,632 B2 | 6/2010 | Usher | |
| 7,794,478 B2 | 9/2010 | Nilsson | |
| 7,799,054 B2 | 9/2010 | Kwak et al. | |
| 7,806,912 B2 * | 10/2010 | Lawton et al. | 606/250 |
| 7,811,310 B2 | 10/2010 | Baker et al. | |
| 2002/0032442 A1 | 3/2002 | Altarac et al. | |
| 2003/0018334 A1 * | 1/2003 | Richelsoph et al. | 606/61 |
| 2006/0052783 A1 | 3/2006 | Dant et al. | |
| 2006/0052786 A1 | 3/2006 | Dant et al. | |
| 2006/0058789 A1 * | 3/2006 | Kim et al. | 606/61 |
| 2006/0064093 A1 | 3/2006 | Thramann et al. | |
| 2006/0217718 A1 | 9/2006 | Chervitz et al. | |
| 2006/0235393 A1 | 10/2006 | Bono et al. | |
| 2006/0271045 A1 | 11/2006 | Hubbard et al. | |
| 2007/0083201 A1 | 4/2007 | Jones et al. | |
| 2007/0213721 A1 | 9/2007 | Markworth | |
| 2007/0213723 A1 | 9/2007 | Markworth | |
| 2007/0233090 A1 | 10/2007 | Naifeh | |
| 2007/0270808 A1 | 11/2007 | Drewry et al. | |
| 2007/0270809 A1 | 11/2007 | Drewry et al. | |
| 2007/0288009 A1 | 12/2007 | Brown et al. | |
| 2008/0021464 A1 | 1/2008 | Morin et al. | |
| 2008/0071273 A1 | 3/2008 | Hawkes et al. | |
| 2008/0091205 A1 | 4/2008 | Kuiper et al. | |
| 2008/0109039 A1 | 5/2008 | Michielli et al. | |
| 2008/0140075 A1 | 6/2008 | Ensign et al. | |
| 2008/0172093 A1 | 7/2008 | Nilsson | |
| 2008/0177315 A1 | 7/2008 | Usher | |
| 2008/0255617 A1 | 10/2008 | Cho et al. | |
| 2008/0306535 A1 | 12/2008 | Winslow et al. | |
| 2008/0312692 A1 | 12/2008 | Brennan et al. | |
| 2009/0105765 A1 * | 4/2009 | Strnad | 606/278 |
| 2009/0318968 A1 | 12/2009 | Duggal et al. | |
| 2010/0160981 A1 | 6/2010 | Butler et al. | |
| 2010/0191289 A1 | 7/2010 | Ludwig et al. | |
| 2010/0204733 A1 | 8/2010 | Rathbun et al. | |
| 2010/0324599 A1 | 12/2010 | Montello et al. | |

FOREIGN PATENT DOCUMENTS

| | | |
|---|---|---|
| EP | 1743585 A1 | 1/2007 |
| WO | 2007/044715 | 4/2007 |
| WO | 2007/127601 | 11/2007 |
| WO | 2008/057217 | 5/2008 |

* cited by examiner

SPINAL CROSS CONNECTOR

CROSS-REFERENCE TO RELATED APPLICATIONS

This is a U.S. Patent Application claiming the benefit of priority under 35 USC 119(e) of commonly owned and U.S. Provisional Patent Application No. 61/221,525 entitled "Systems and Methods for Anterior Fixation of the Spine," filed Jun. 29, 2009, and U.S. Provisional Patent Application No. 61/233,287 entitled "Spinal Cross Connector," filed Aug. 12, 2009, the entire contents of which are hereby expressly incorporated by reference into this disclosure as if set forth fully herein.

FIELD OF THE PRESENT INVENTION

The disclosed system and associated methods relate to spinal instrumentation for use and implantation during spine surgery.

BACKGROUND

The spine is formed of a column of vertebrae that extends between the cranium and pelvis. The five sections of the spine are the cervical, thoracic, lumbar, sacral, and coccygeal regions. There are 7 cervical, 12 thoracic, 5 lumbar, 5 sacral, and 4 coccygeal vertebrae. Cervical, thoracic, and lumbar vertebra are separated from one another by intervertebral discs that absorb shock, allow for movement, and maintain appropriate spacing between the vertebrae. The main functions of the spine include providing skeletal support and protecting the spinal cord. Even slight disruptions to either the intervertebral discs or vertebrae can result in serious discomfort due to compression of nervous tissue within or extending from the spinal canal. If a disruption to the spine becomes severe enough, consequences may include pain, loss of sensation, paralysis, etc. . . . Thus, it is of great interest and concern to be able to both prevent and correct ailments of the spine.

Surgical intervention, when needed, for treating various spinal ailments often entails fixing two or more vertebrae relative to each other. Spinal fixation constructs often use a combination of rods, plates, pedicle screws and bone hooks for constructing a rigid framework and anchoring it to the affected vertebrae. The optimal configuration required for each patient varies according to the patient's anatomical characteristics, the specific ailment being treated, and surgeon preference, among other factors. At times, the strength and stability of these custom configurations may be compromised as a result of torsional forces placed on the rods that span two or more vertebrae.

Spinal cross connectors are often implanted horizontally between two vertical rods to provide extra stability and decrease the torsional forces acting upon the rods in the customized surgical construct. Implantation of some spinal cross connectors known in the prior art can be time-consuming because locking more than one locking mechanism is required. Needs still exist for modular spinal fixation systems and components that provide maximum strength and stability in an easy-to-use fashion.

DETAILED DESCRIPTION

Figure 1:
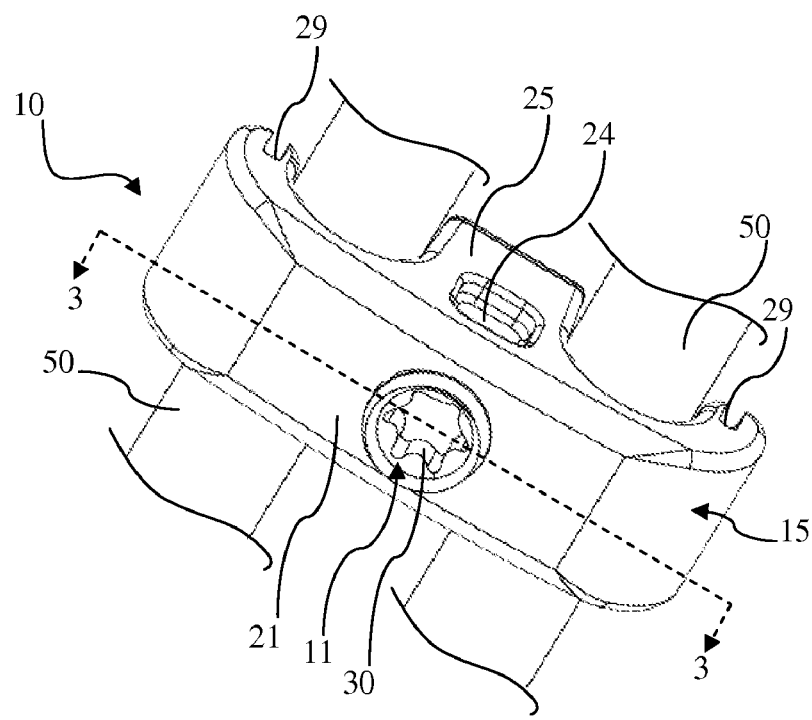
FIG. 1 is a front perspective view of a spinal cross connector assembly engaging two rods, according to one example embodiment.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The cross connector assembly disclosed herein boasts a variety of inventive features and components that warrant patent protection, both individually and in combination.

FIGS. 1-6 illustrate a cross connector assembly 10 according to one example embodiment. The cross connector assembly 10 is sized and dimensioned to be attached to two elongate members (e.g. rods 50), fixed generally parallel to each other across at least one spinal segment. The cross connector assembly provides additional support to the two elongate members, particularly in resisting torsional stress. The cross connector assembly 10 includes a set screw 11, an adjustable wedge 12, a housing 15, a closure plate 14, and a set of securing blocks 13. Preferably, the cross connector assembly 10 is composed of a surgical-grade metal (e.g. titanium, stainless steel, etc. . . . ), but may also be composed of a surgical-grade polymer (e.g. poly-ether-ether-ketone (PEEK)) or any other material suitable for the applications of the present invention. Additionally, the cross connector assembly 10 may be composed of a combination of both metal and polymer materials.

The housing 15 includes at least one tool engaging feature 24 situated along the first and second side surfaces 25, 26 of the housing 15 for enabling the engagement of a variety of tools. These tools can be used to assist in the placement of the cross connector assembly 10 during a surgical procedure. The housing 15 further includes a cavity 20 which extends generally perpendicular into the housing 15 from the front surface 21. The cavity 20 includes at least one internal thread 22 for threadably receiving the set screw 11 into the housing 15. The advancement of the set screw 11 into the housing 15 facilitates securing the elongate members to the housing 15, as will be described in greater detail below.

Additionally, the housing 15 includes two arched recesses 23 that are each shaped and dimensioned to allow the secure reception of an elongate member (e.g. rod 50). Although the arched recesses 23 are arched in this example, it will be appreciated that the size and shape of the recess may be adapted to complement non-cylindrical rods as well. Permanently securing the elongate members within the arched recesses 23 involves the radial translation of the securing blocks 13 within the housing 15, such that they are forced out towards the elongate members. The radial translation of the securing blocks 13 is caused by advancement of the set screw 11, as will be discussed in more detail below.

Figure 5:
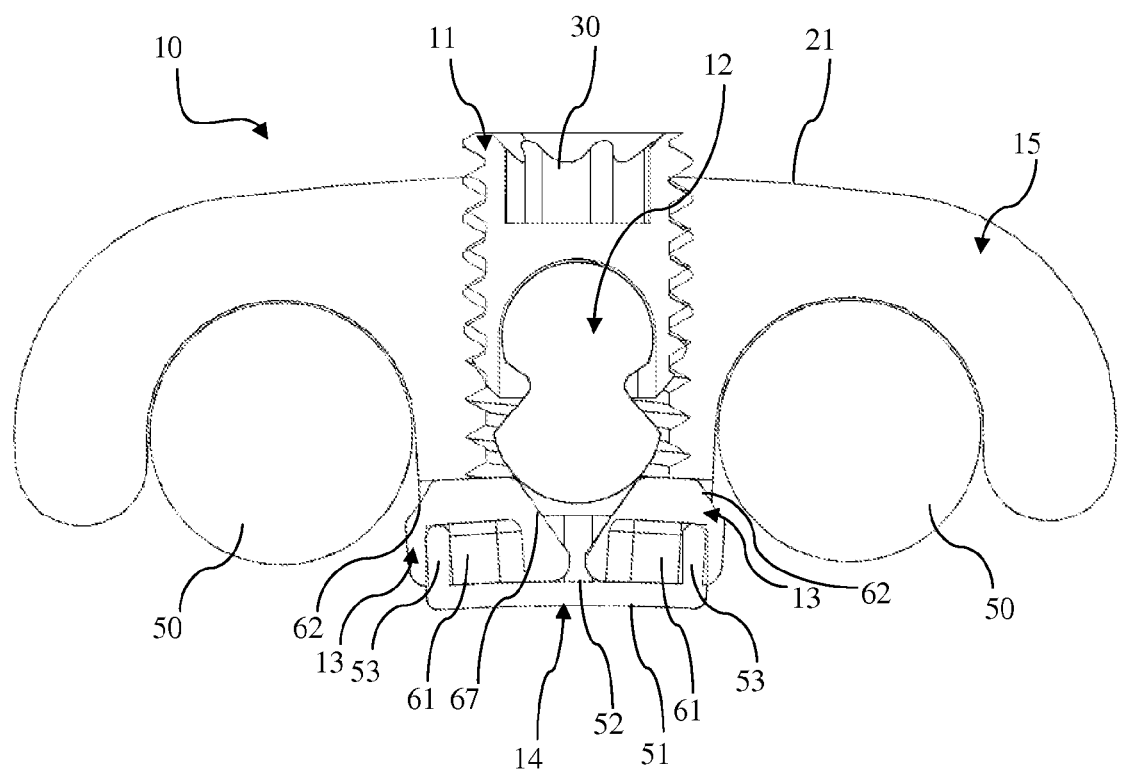
FIG. 5 is a side view cross section of the cross connector assembly of FIG. 3.
Figure 7:
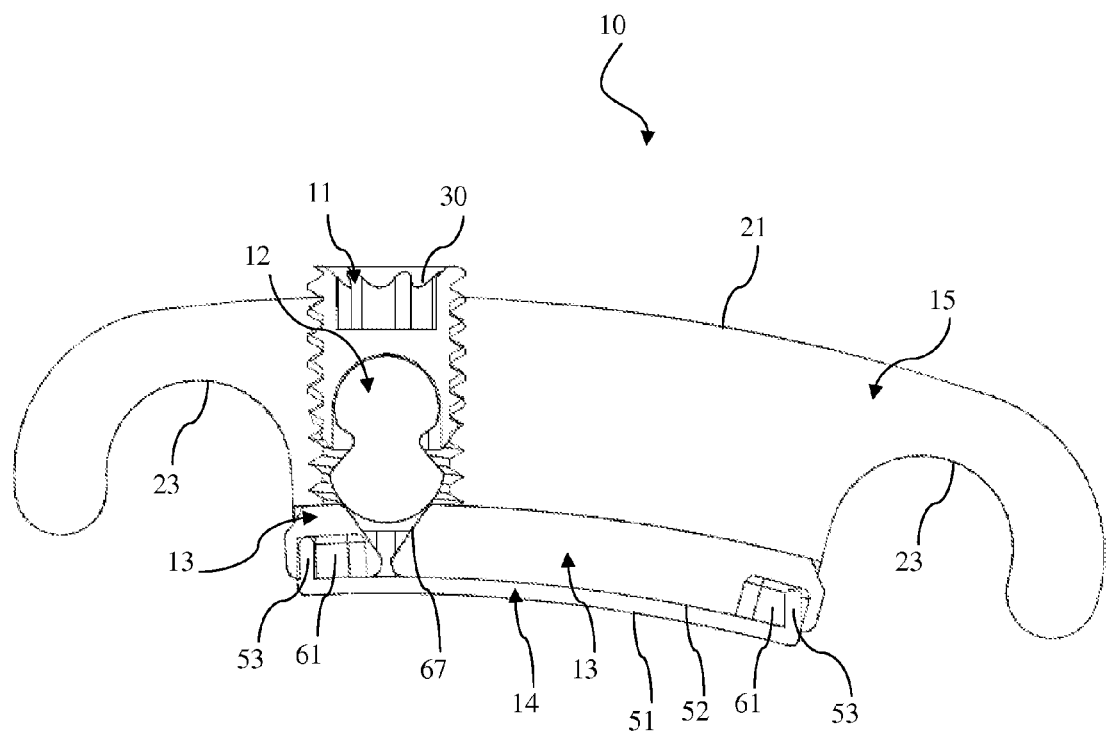
FIG. 7 is a side view cross section of a cross connector assembly, according to a second embodiment.

A closure plate 14 may be secured at the base 18 of the housing 15 and may be provided with a radial profile along its interior and exterior surfaces 52, 51 so that when the cross connector assembly 10 is viewed from the top or bottom (as best illustrated in FIG. 5 and FIG. 7) the exterior surface 51 of the closure plate 14 is generally concave. The concave feature of the cross connector assembly 10 allows the closure plate 14 to avoid unnecessary dural impingement once the cross connector assembly 10 is implanted, particularly when the cross connector assembly 10 is assembled to a posterior spinal fixation assembly. It is also contemplated that the cross connector assembly may not have a closure plate 14. In such an embodiment, the securing blocks 13 may be contained and guided by pins or other suitable retaining mechanisms.

Figure 3:
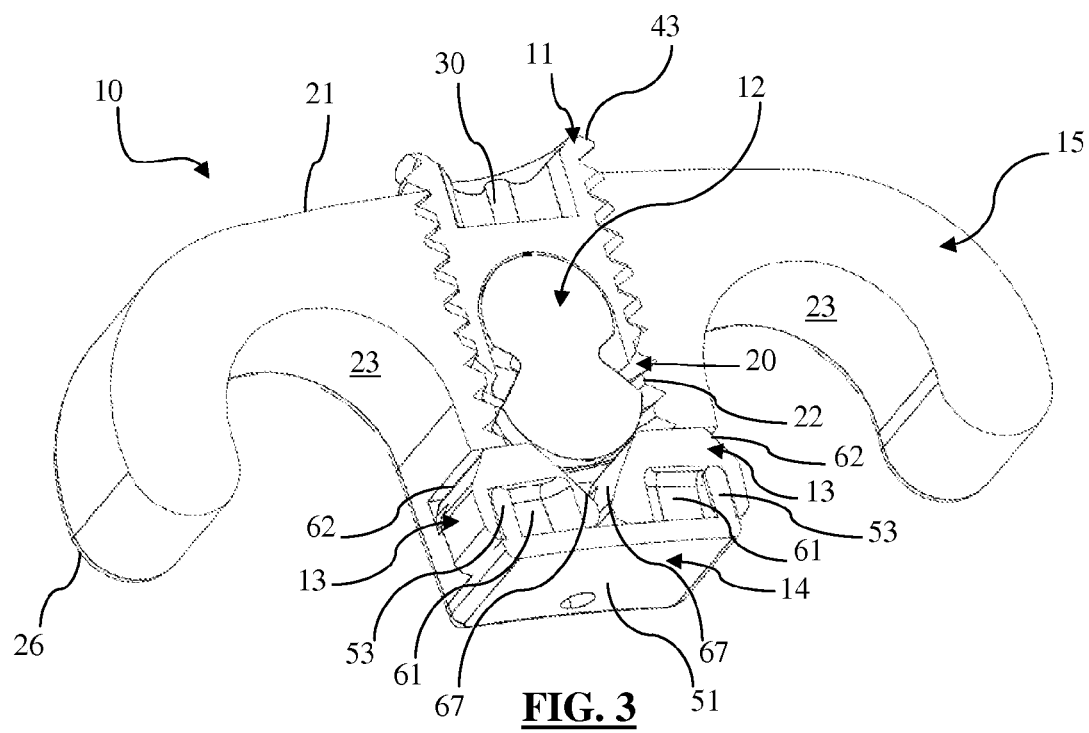
FIG. 3 is a cross section view of the cross connector assembly taken along line 3-3 of FIG. 1.
Figure 4:
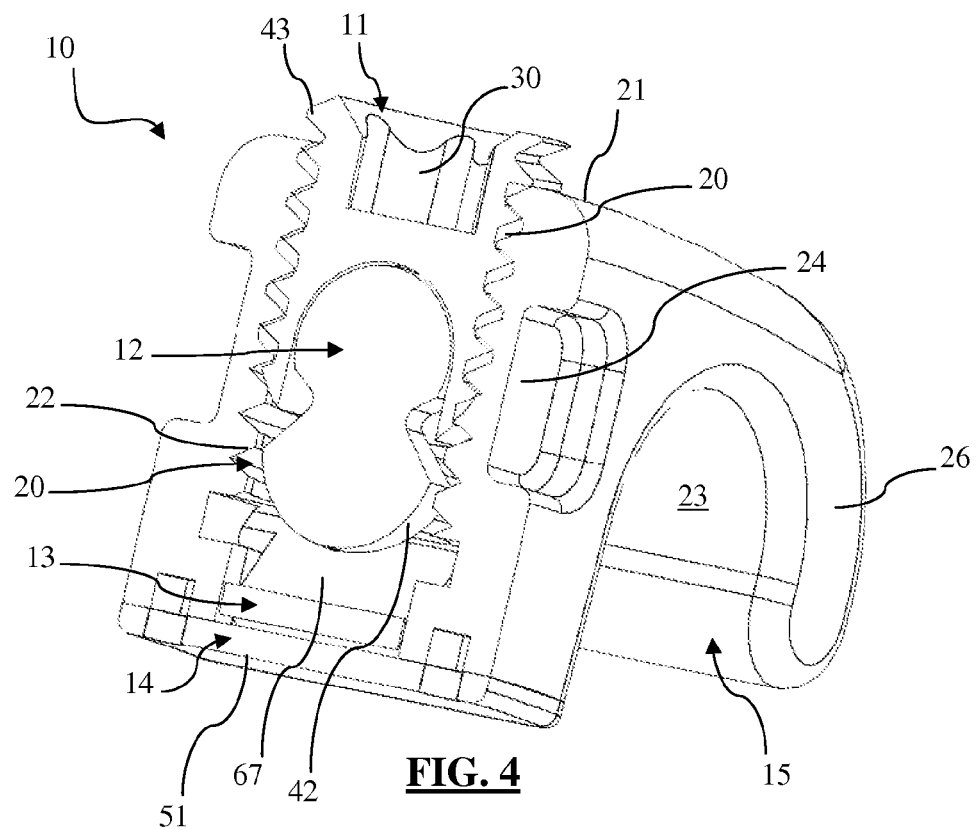
FIG. 4 is a cross section view of the cross connector assembly taken along line 4-4 of FIG. 2.
Figure 6:
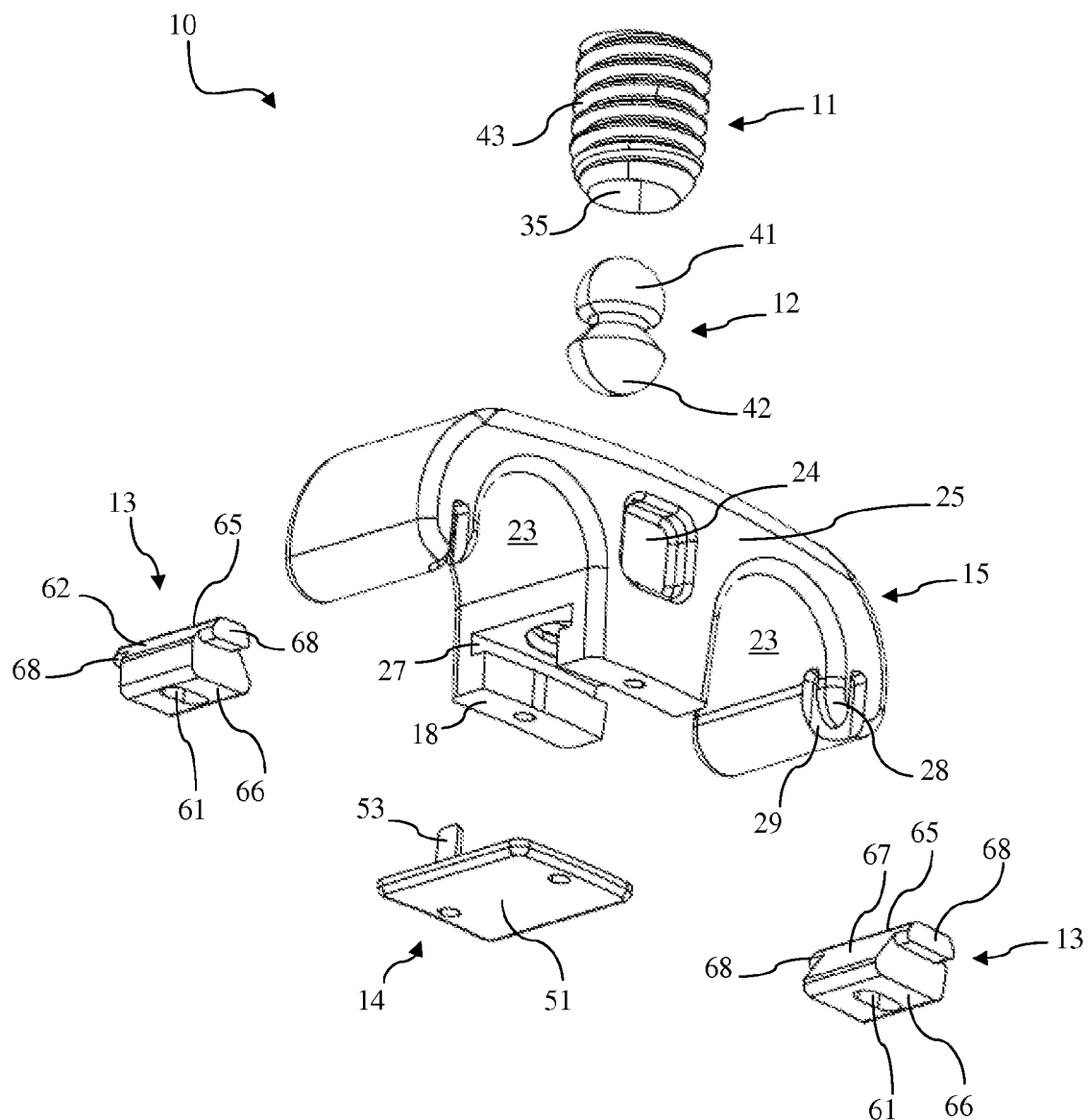
FIG. 6 is an exploded view of the cross connector assembly of FIG. 1.

The internal surface 52 of the closure plate 14 includes at least two bumpers 53 which extend at least partially along the internal surface 52 of the closure plate 14 and interact with the positioning cavities 61 of the securing blocks 13 (as best illustrated in FIGS. 3 and 6). The bumpers 53 at least partially function to assist in the positioning of the securing blocks 13. Radial translation of the securing blocks 13 is at least partially guided by the radial indented slots 27 (as best shown in FIG. 6) within the housing 15.

Securing blocks 13 frictionally engage the elongate members at their engagement surfaces 62. The engagement surface 62 of the securing block 13 and/or the surfaces within the arched recesses 23 may have surface features, or surface roughening, to enhance the frictional engagement between the cross connector assembly 10 and elongate members for secure positioning. The cross connector assembly 10 is preferably provided in multiple sizes for versatility. The housing 15 may be dimensioned, for example, so that the distance between the center of the first arched recess 23 and the center of the second arched recess 23 is approximately within the range of about 11-80 mm.

The securing blocks 13 include a tapered surface 67 which allows the spherical wedge 42 of the adjustable wedge 12 to apply force onto the securing block 13 and force the securing block 13 to translate towards the arched recess 23. Wings 68 extend out from both sides of the securing blocks 13 and mate with indented slots 27 within the housing 15. The indented slots 27 provide a pathway for the wings 68 to travel through the housing 15 and assist in maintaining proper alignment of the securing blocks 13. The indented slots 27 are radially disposed so that the wings 68 (which may also have a radial side profile) guide the translation of the securing blocks 13 radially through the housing 15.

The set screw 11 of the cross connector assembly 10 includes a generally recessed tool engagement feature 30 centrally located at a first end which functions to engage a variety of tooling that assist in advancing the set screw 11 into the housing 15. Centrally located at a second end of the set screw 11 is a spherical recess 35. The spherical recess 35 provides a socket for the spherical joint end 41 of the adjustable wedge 12, such that the adjustable wedge 12 and set screw 11 interact similar to a ball and socket joint. At least one exterior thread 43 radially extends from the outer surface of the set screw 11 for threaded advancement into the housing 15. Upon advancement of the set screw 11 along its central axis into the housing 15, the spherical recess 35 pushes against the spherical joint end 41 of the adjustable wedge 12. As the adjustable wedge 12 is forced in the direction of the securing blocks 13, the adjustable wedge 12 swivels within the spherical recess 35 to align and compress the spherical wedge 42 evenly between the pair of securing blocks 13.

The adjustable wedge 12 includes a spherical joint end 41 which, as described above, mates and interacts with the spherical recess 35 of the set screw 11. During assembly of the cross connector assembly 10, the spherical joint end 41 is mated with the spherical recess 35 of the set screw 11. The circumferential distal end of the set screw 11 may be then slightly bent inward so that the spherical joint end 41 of the adjustable wedge 12 is unable to completely disengage from the set screw 11 while still allowing the adjustable wedge 12 to freely rotate and articulate. At the opposite end of the adjustable wedge 12 is the spherical wedge 42 which rests in contact with the tapered surfaces 67. The ability of the spherical wedge 42 to align itself evenly between the tapered surfaces 67 (by way of the spherical joint end 41 swiveling in the spherical recess 35) allows the spherical wedge 42 to distribute force evenly between the pair of securing blocks 13. Radial translation of the securing blocks 13 thus occurs evenly, even in the presence of geometric variations (e.g. machining, tolerances, etc.) that could otherwise result in the uneven application of force to the securing blocks 13, and ultimately to the elongate members. The adjustable wedge 12 thus ensures even force is applied to each of the securing blocks 13, resulting in equal compression on the elongate members and secure engagement therein.

FIG. 7 illustrates another embodiment of the present cross connector assembly 10 wherein the radial curvature of at least the closure plate 14, indented slots 27, and top and bottom surfaces 65, 66 of the securing blocks 13 can be observed. As mentioned above, the radial curvature of the closure plate 14 assists in avoiding dural impingement once the cross connector assembly 10 is implanted, particularly when the cross connector assembly 10 is assembled to a posterior spinal fixation assembly. Additionally, this embodiment illustrates the possibility for the set screw 11 and adjustable wedge 12 to be positioned offset from the center of the housing 15, without deviating from the scope of the invention. Accordingly, the securing blocks 13 assembled within the housing 15 may be dimensioned differently depending upon the desired set screw 11 positioning.

Figure 2:
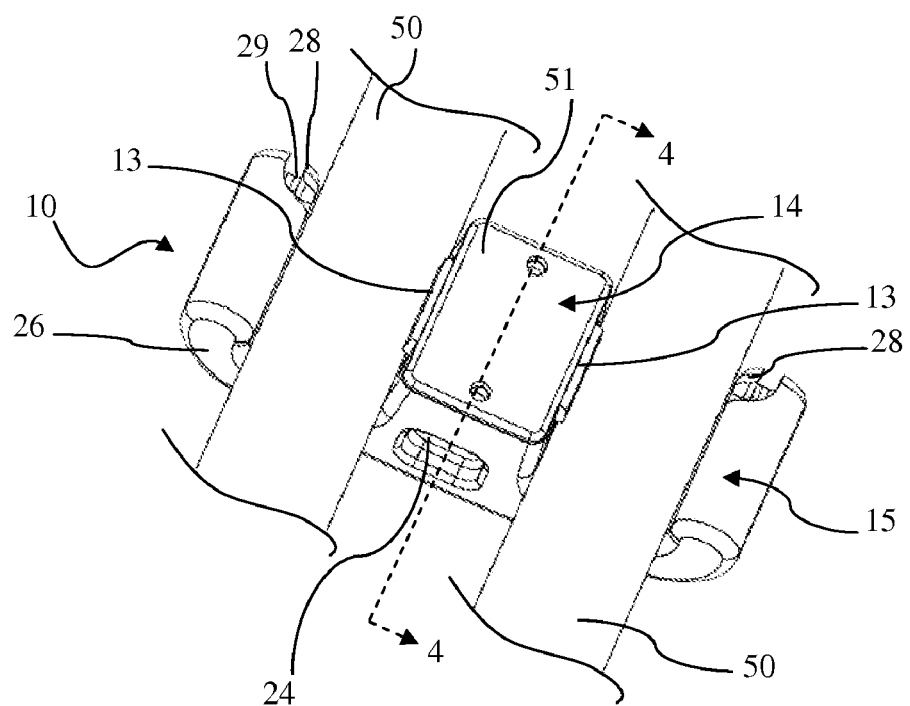
FIG. 2 is a back perspective view the cross connector assembly of FIG. 1 engaged with a pair of rods.

FIGS. 1, 2, and 5 illustrate an example embodiment of a cross connector assembly 10 assembled to a pair of elongate structures (e.g. rods 50) which make up at least a part of a spinal fixation assembly (not shown). Preferably, the cross connector assembly 10 is inserted laterally into a patient's spine and assembled to elongate members that make up at least a portion of a lateral spinal fixation assembly. For example, once a pair of rods 50 are surgically implanted and positioned such that they are generally parallel to each other along at least a portion of a lateral aspect of the spine, the cross connector assembly 10 can then be assembled to the pair of rods 50. It is envisioned that the cross connector assembly 10 may also be sized and dimensioned to be inserted posteriorly into a patient's spine and assembled to elongate members that make up at least a portion of a posterior spinal fixation assembly. For example, once a pair of rods 50 are surgically implanted and positioned such that they are generally parallel to each other along at least a portion of a posterior aspect of the spine, the cross connector assembly 10 can then be assembled to the pair of rods 50.

To assemble the cross connector 10 to a pair of rods, a first arched recess 23 of the cross connector 10 is aligned and placed over a section of a first rod 50. Then a second arched recess 23 of the cross connector is aligned and placed over a section of the second rod 50.

The cross connector assembly 10 may be provided with machined slots 29 located at the distal end of each of the arched recesses 23 which form tabs 28. The tabs 28 may be slightly bent inward (not shown) toward the arched recess 23. The bent tab 28 deflects outward as the elongate member passes. Once an elongate member clears the tab 28, the bent tab 28 returns to its original formation which produces a tactile indication to the user that the elongate member is positioned completely within the arched recess 23. Additionally, the tab 28 assists in retaining the elongate member 50 within the arched recess 23 until the user is able to permanently secure the elongate members 50 with the set screw 11.

The cross connector assembly 10 may be provided with the set screw 11 pre-engaged in an un-secured position into the housing 15. When the cross connector assembly 10 is in the desired position along the rods 50, tooling can be used to engage the tooling feature 30 at the exposed end of the set screw 11 and advance the set screw 11 in the direction of the securing blocks 13 within the housing 15. As the set screw 11 is advanced towards the securing blocks 13, the spherical recess 35 applies a force onto the spherical joint 41 of the adjustable wedge 12. The applied force delivered by the set screw 11 onto the adjustable wedge 12 is a linear force directed along the centerline of the set screw 11. As described above, the spherical joint 41 of the adjustable wedge 12 swivels within the spherical recess 35 to situate itself and equal force is transferred to the rods 40 and the rods 50 become securely engaged in the cross connector assembly 10. Once the cross connector assembly 10 is securely engaged to the rods 50, the engagement tool used to advance the set screw 11 can be disengaged from the tooling feature 30 and the cross connector assembly 10 can be left to remain permanently implanted. In the event the cross-connector needs to be removed, the set screw may be retracted back to the unlocked position, releasing the force on the securing blocks 13 such that the cross connector assembly 10 may then be pulled off of the elongate members.

While not specifically described above, it will be understood that various other steps may be performed in using and implanting the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor following insertion of the implant, and closing the surgical wound. Furthermore, procedures described, for example only, may be applied to any region of the spine without departing from the scope of the present invention and dimensioning of the implant may be adjusted to accommodate any region.

While this invention has been described in terms of a best mode for achieving this invention's objectives, it will be appreciated by those skilled in the art that variations may be accomplished in view of these teachings without deviating from the spirit or scope of the invention.

I claim:

1. A spinal cross connector, comprising:
a housing member having a central portion with a top, a base, and opposing first and second sides, wherein said base includes two longitudinal indented slots extending from said first and second opposing sides;
a threaded aperture situated on said top;
first and second rod channels adjacently disposed to said first and second opposing sides of said housing member;
a locking screw advancable within said threaded aperture and having a spherical recess at a lower end; and
a swivel member having a first end disposed within said spherical recess and a second end that bears on each of said first and second rod-stabilization members.

2. The spinal cross connector of claim 1, wherein said first and second rod channels are formed in a bottom surface of said housing member.

3. The spinal cross connector of claim 1, wherein said rod-stabilization members independently and simultaneously engage spinal fixation rods placed within said first and second rod channels.

4. The spinal cross connector of claim 1, wherein said swivel member is an adjustable wedge comprising a spherical joint end mated to said spherical recess of said locking screw.

5. The spinal cross connector of claim 1, wherein said swivel member and said locking member cooperate to effect radial translation of said first and second rod-stabilization members such that the first and second rod-stabilization members simultaneously engage with spinal fixation rods situated within said first and second rod channels.

6. The spinal cross connector of claim 1, wherein each of said rod-stabilization members further include a medial tapered surface upon which said adjustable wedge bears.

7. The spinal cross connector of claim 1, wherein said longitudinal intended slots are radially disposed within said base.

8. The spinal cross connector of claim 7, wherein each of said rod-stabilization members include lateral extension elements slideably disposed within said longitudinal indented slots.

* * * * *